United States Patent
Nakanishi (10) Patent No.: US 9,737,277 B2
(45) Date of Patent: Aug. 22, 2017

(54) X-RAY CT SYSTEM AND MEDICAL IMAGE PROCESSING METHOD

(71) Applicant: Toshiba Medical Systems Corporation, Otawara-shi (JP)

(72) Inventor: Satoru Nakanishi, Arlington Heights, IL (US)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/262,332

(22) Filed: Apr. 25, 2014

(65) Prior Publication Data

US 2014/0233695 A1    Aug. 21, 2014

Related U.S. Application Data

(63) Continuation of application No. PCT/JP2013/073792, filed on Sep. 4, 2013.

(30) Foreign Application Priority Data

Sep. 10, 2012 (JP) .................................. 2012-198052
Aug. 29, 2013 (JP) .................................. 2013-178459

(51) Int. Cl.
*A61B 6/00* (2006.01)
*G06T 3/00* (2006.01)
(Continued)

(52) U.S. Cl.
CPC .......... *A61B 6/5235* (2013.01); *A61B 6/5205* (2013.01); *A61B 6/5211* (2013.01);
(Continued)

(58) Field of Classification Search
CPC ....... A61B 6/52; A61B 6/5211; A61B 6/5229; A61B 6/5235; A61B 6/5241;
(Continued)

(56) References Cited

U.S. PATENT DOCUMENTS 5,802,133 A    9/1998  Kawai et al.
5,974,108 A   10/1999  Taguchi et al.
(Continued)

FOREIGN PATENT DOCUMENTS

CN    101756707 A    6/2010
CN    102124320 A    7/2011
(Continued)

OTHER PUBLICATIONS

International Search Report issued on Dec. 17, 2013 for PCT/JP2013/073792 filed on Sep. 4, 2013 with English Translation.
(Continued)

*Primary Examiner* — Anastasia Midkiff
(74) *Attorney, Agent, or Firm* — Oblon, McClelland, Maier & Neustadt, L.L.P.

(57) ABSTRACT

An X-ray CT system and a method of processing medical images are provided that enable combining of images with reduced effect of the differences in coordinates of the pixels in the overlapped areas of a plurality of constituent images. The X-ray CT system includes a processor and a synthesizer. Based on coordinates of first pixels in a first image of a first three-dimensional region of the subject and coordinates of second pixels in a second image of a second three-dimensional region of the subject, the processor combines the first pixels with the second pixels on a one-for-one basis within a predetermined range in the rostrocaudal direction. The synthesizer generates third pixels relative to the first pixels and the second pixels and generates a third image that includes the third pixels.

12 Claims, 4 Drawing Sheets

(51) Int. Cl.
*A61B 6/03* (2006.01)
*A61B 6/02* (2006.01)

(52) U.S. Cl.
CPC .......... *A61B 6/5229* (2013.01); *G06T 3/0056* (2013.01); *G06T 3/0068* (2013.01); *A61B 6/027* (2013.01); *A61B 6/032* (2013.01); *A61B 6/5241* (2013.01)

(58) Field of Classification Search
CPC A61B 6/5258; G06T 1/00; G06T 3/00; G06T 3/0056; G06T 3/0068; G06T 3/40; G06T 3/4038; G06T 5/00; G06T 5/50; G06T 7/00; G06T 7/0022; G06T 7/0024; G06T 7/0026; G06T 7/0028; G06T 7/0034; G06T 7/0038; G06T 7/0079; G06T 7/0097; G06T 2200/00; G06T 2200/04; G06T 2200/32; G06T 2207/00; G06T 2207/20112; G06T 2207/20136; G06T 2207/20141; G06T 2207/20212; G06T 2207/20221; G06T 2211/00; G06T 2211/40; G06K 9/00; G06K 9/0026; G06K 9/34; G06K 9/342; G06K 9/60; G06K 9/62; G06K 9/6201; G06K 9/6202; G06K 9/6203; G06K 9/6212; G06K 9/64; G06K 2009/2045; G06K 2009/6213
See application file for complete search history.

(56) References Cited

U.S. PATENT DOCUMENTS

| | | | | |
|---|---|---|---|---|
| 6,516,046 | B1* | 2/2003 | Frohlich | A61B 6/04 378/205 |
| 8,731,267 | B2* | 5/2014 | Nakanishi | A61B 6/032 382/131 |
| 2002/0090058 | A1* | 7/2002 | Yasuda | A61B 6/08 378/205 |
| 2006/0029285 | A1* | 2/2006 | Hein | G06T 5/50 382/260 |
| 2006/0222260 | A1* | 10/2006 | Sambongi | G06T 5/50 382/274 |
| 2007/0036410 | A1 | 2/2007 | Ida et al. | |
| 2008/0002806 | A1 | 1/2008 | Nishide et al. | |
| 2009/0268867 | A1 | 10/2009 | Mori et al. | |
| 2010/0204562 | A1* | 8/2010 | Gorges | A61B 6/0457 600/407 |
| 2011/0075905 | A1* | 3/2011 | Noshi | A61B 6/032 382/131 |
| 2012/0219201 | A1 | 8/2012 | Ida et al. | |
| 2013/0251223 | A1* | 9/2013 | Smith | G06T 5/20 382/131 |

FOREIGN PATENT DOCUMENTS

| | | |
|---|---|---|
| CN | 102184560 A | 9/2011 |
| CN | 102316806 A | 1/2012 |
| JP | 5-154141 A | 6/1993 |
| JP | 6-70924 A | 3/1994 |
| JP | 9-149902 A | 6/1997 |
| JP | 2002-136507 A | 5/2002 |
| JP | 2002-186605 A | 7/2002 |
| JP | 2003-275201 A | 9/2003 |
| JP | 2006-43431 A | 2/2006 |
| JP | 2007-68554 A | 3/2007 |
| JP | 2007-97754 A | 4/2007 |
| JP | 2008-6032 A | 1/2008 |
| JP | 2011-72400 A | 4/2011 |
| JP | 2012-55393 A | 3/2012 |
| JP | 2012-179373 A | 9/2012 |

OTHER PUBLICATIONS

Combined Office Action and Search Report issued on Nov. 3, 2015 in Chinese Patent Application No. 201380004435.7 with English translation of category of cited documents.
Office Action issued on Feb. 7, 2017 in Japanese Patent Application No. 2013-178459.

* cited by examiner

X-RAY CT SYSTEM AND MEDICAL IMAGE PROCESSING METHOD

CROSS-REFERENCE TO RELATED APPLICATION

This application is based upon and claims the benefit of priority from Japanese Patent Applications No. 2012-198052 filed on Sep. 10, 2012 and No. 2013-178459, filed on Aug. 29, 2013; the entire contents of which are incorporated herein by reference.

FIELD

Embodiments relate to X-ray CT systems and methods of processing medical images.

BACKGROUND

X-ray CT (Computed Tomography) systems are a type of equipment that provides imaging of the interior of a subject by scanning the subject with X-rays for data acquisition and then by processing the acquired data with a computer.

An X-ray CT system comprises a revolving module of an X-ray tube and an X-ray detector, which are mounted facing each other on a circular ring-like frame, and the scanning of a subject positioned inside the frame is performed, with the revolving module being rotated, by radiating X-rays from the X-ray tube and by detecting X-rays that have passed through the subject with the X-ray detector.

Among scanning methods performed by X-ray CT systems, there is a scanning method called "step and shoot". This method obtains an image that covers a broad range of the subject by the following steps: at first, a part of the subject is irradiated with X-rays and scanned into an image; then the X-ray radiation is stopped momentarily, and without X-ray irradiation, the subject together with the bed is moved by a predetermined distance in the rostrocaudal direction; then another part of the subject is irradiated with X-rays and scanned into an image; and with the cycle of translation and scanning having been repeated, the images of all the scanned parts of the subject are combined into a whole. Generally, the images of the scanned parts of the subject have some areas that overlap one another, and the overlapped areas in image are rendered with feathering. Feathering is a process that makes changes in pixel values moderate near the boundaries between the overlapped areas and the other parts of the images, which are overlapping each other.

DETAILED DESCRIPTION

The X-ray CT system of this embodiment comprises: a couch; a radiator; a detector; an image generator; a processor; and a synthesizer.

The couch is configured to be mounted with a subject and to be translated in the rostrocaudal direction of the subject. The radiator is configured to irradiate the subject mounted on the couch with X-rays. The detector is configured to detect X-rays that have passed through the subject, of the X-rays radiated by the radiator. The image generator is configured to generate an image that represents a three-dimensional region of the subject, based on data detected by the detector. The processor is configured to combine, based on the coordinates of a first pixel in a first image that the image generator has generated about a first three-dimensional region of the subject and the coordinates of a second pixel in a second image generated about a second three-dimensional region of the subject, the first pixel with the second pixel on a one-for-one basis within a predetermined range in the rostrocaudal direction. The synthesizer is configured to generate a third pixel relative to the first pixel and the second pixel constituting the combination by the processor and to generate a third image that includes the third pixel.

A method of processing medical images processes medical images between a first image about a first three-dimensional region of a subject and a second image about a second three-dimensional region of the subject, the images having been generated by an X-ray CT system comprising a couch, on which the subject is mounted and moved in the rostrocaudal direction of the subject.

The method comprises: combining, based on the coordinates of a first pixel in the first image and the coordinates of a second pixel in the second image, the first pixel with the second pixel on a one-for-one basis within a predetermined range in the rostrocaudal direction; generating a third pixel relative to the first pixel and the second pixel constituting the combination; and generating a third image that includes the third pixel.

Now, an X-ray CT system as an embodiment is described with reference to the drawings.

[Configuration]

Figure 1:
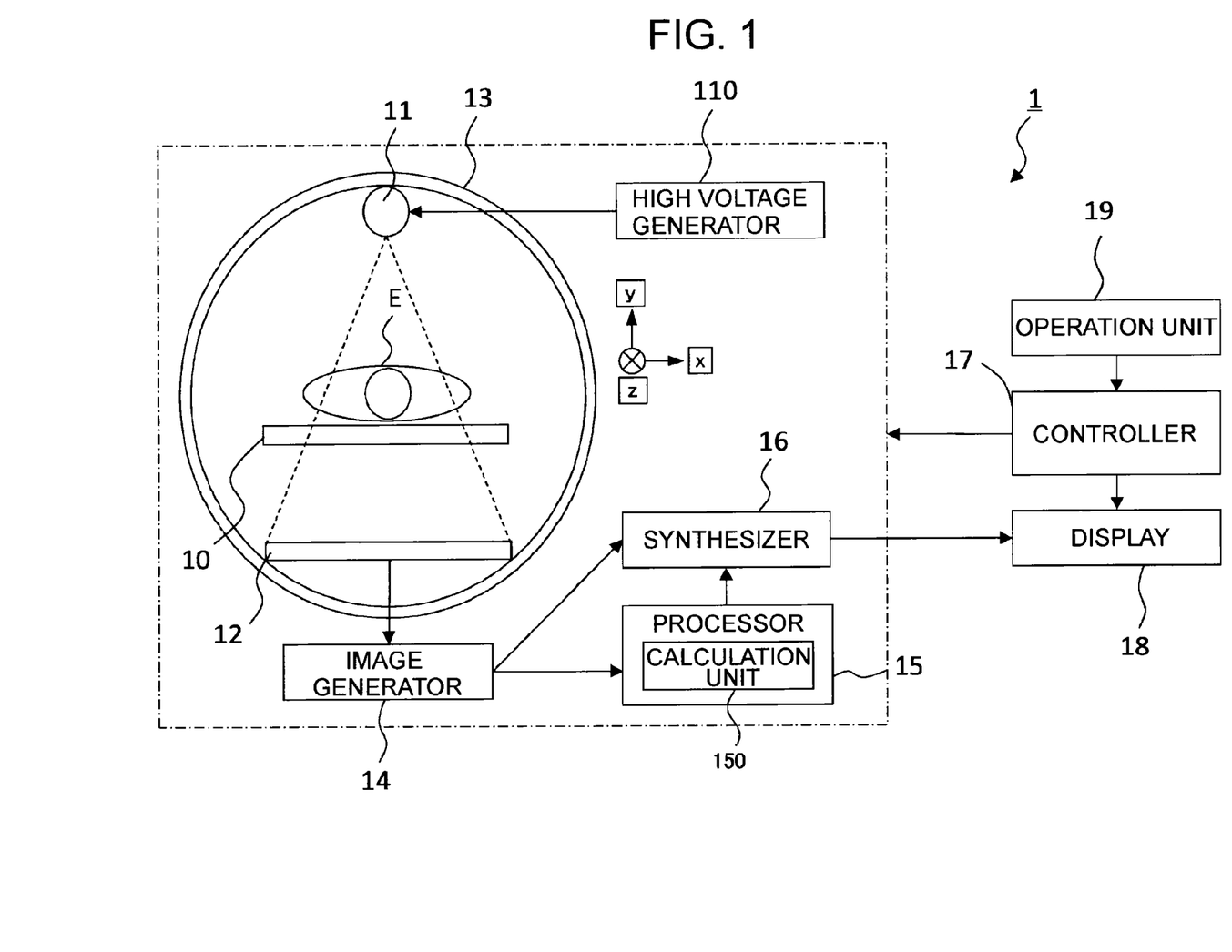
FIG. 1 is a block diagram showing the configuration of an X-ray CT system as an embodiment.

FIG. 1 is a block diagram representing the configuration of the X-ray CT system 1 as an embodiment. Incidentally, since the terms "image" and "image data" correspond to each other one-on-one, they may be used as identical terms.

The X-ray CT system 1 comprises a couch 10, a radiator 11, a high voltage generator 110, a detector 12, a revolving module 13, an image generator 14, a processor 15, a synthesizer 16, a controller 17, a display 18, and an operation unit 19.

(Couch 10)

The couch 10 is mounted with a subject E and is moved in the rostrocaudal direction of the subject E. In addition, the couch 10 may be moved in the up and down direction (i.e., in the direction of axis y).

(Radiator 11)

The radiator 11 irradiates the subject E mounted on the couch 10 with X-rays. The radiator 11 may comprise an ordinary X-ray tube (e.g., a vacuum tube that generates a beam in circular cone or in pyramid shape; not shown).

(High Voltage Generator 110)

The high voltage generator 110 supplies a high voltage to the radiator 11, and the radiator 11 generates X-rays based on the high voltage.

(Detector 12)

The detector 12 detects X-rays that have passed through the subject E of the X-rays radiated by the radiator 11. The detector 12 may comprise a plurality of X-ray detector elements (not shown). The detector 12 detects, with its X-ray detector elements, X-ray intensity distribution data (hereinafter referred to also as "detection data"), which show the intensity distribution of the X-rays that have passed through the subject E, and then the detector 12 outputs the detection data in current signals.

The detector 12 comprises a two-dimensional X-ray detector (area detector) in which, for example, a plurality of detector elements are disposed, respectively, in two inter-orthogonal directions (slicing direction and channeling direction). The X-ray detector elements are aligned, for example, in 320 lines in the slicing direction. The use of an X-ray detector having such a multi-line configuration enables the scanning of a three-dimensional region with a particular width in the slicing direction, per scanning rotation (volumetric scanning). By the way, the slicing direction corresponds to the rostrocaudal direction of the subject E while the channeling direction corresponds to the revolving direction of the radiator 11.

(Revolving Module 13)

The revolving module 13 comprises a member that supports the radiator 11 and the detector 12 facing each other, with the subject E to be positioned between them. The revolving module 13 has a through-opening in the slicing direction, into which the couch 10 mounted with the subject E is inserted. The revolving module 13 revolves around the subject E as its center along a circular orbit. As a result, both the radiator 11 and the detector 12 also revolve around the subject E.

(Image Generator 14)

The image generator 14 generates an image that represents a three-dimensional region of the subject E, based on the data detected by the detector 12. The image generator 14 converts the detection data (current signals) into voltage signals, which are integrated periodically for amplification and are converted into digital signals. The image generator 14 then executes reconstruction-processing on the digital signals for obtaining CT image data (tomographic data and volumetric data), which represent some internal structures of the subject E.

In the reconstruction-processing, the image generator 14 at first executes preprocessing on the digital signals to generate projection data, the preprocessing including logarithmic transformation, offset correction, sensitivity correction, beam-hardening correction, etc. The image generator 14 then generates CT image data (tomographic data and volumetric data) based on the projection data. As reconstruction-processing for tomographic data, such methods as two-dimensional Fourier transformation and convolution-back-projection can be applied arbitrarily. Volumetric data are generated by interpolating plural sets of tomographic data, which have been reconstructed. For volumetric data reconstruction, such methods as cone-beam reconstruction, multi-slice reconstruction, and magnified reconstruction can be employed arbitrarily. Volumetric scanning executed with the above-mentioned multi-line X-ray detector enables reconstruction of volumetric data that cover a wide range.

The reconstruction-processing is executed based on preset reconstruction conditions, which can include various items (and may be referred to also as "condition items"). Examples of the condition items are FOV (field of view), reconstruction function, etc. FOV is a condition item that defines the size of the field of view. The reconstruction function is a condition item that defines such picture characteristics as contrast and resolution. The reconstruction conditions may be set automatically or manually. As an example of automatic setting, there is a method of selectively applying preset contents in correspondence to the specification of a region to be scanned, the preset contents having been predetermined for the region. An example of manual setting is a method in which a setup screen with predetermined reconstruction conditions is displayed on the display 18, and the reconstruction conditions are modified on the setup screen with the operation unit 19. The setting up of FOV is performed by referring to an image or a scanogram based on the projection data. Also, a predetermined FOV can be set automatically (e.g., in the case where the entire scanning range is set as FOV).

The image generator 14 can execute, for example, MPR processing and volume rendering. MPR processing is an image-rendering method for generating MPR image data that represent a view along a particular sectional plane set through volumetric data, which have already been generated. Volume rendering is an image-processing method for generating pseudo-three-dimensional image data by sampling a set of volumetric data along an arbitrary eyeline (ray) and adding their values (CT values), and the pseudo-three-dimensional image data here represents a three-dimensional region of the subject E.

(Processor 15)

Figure 2:
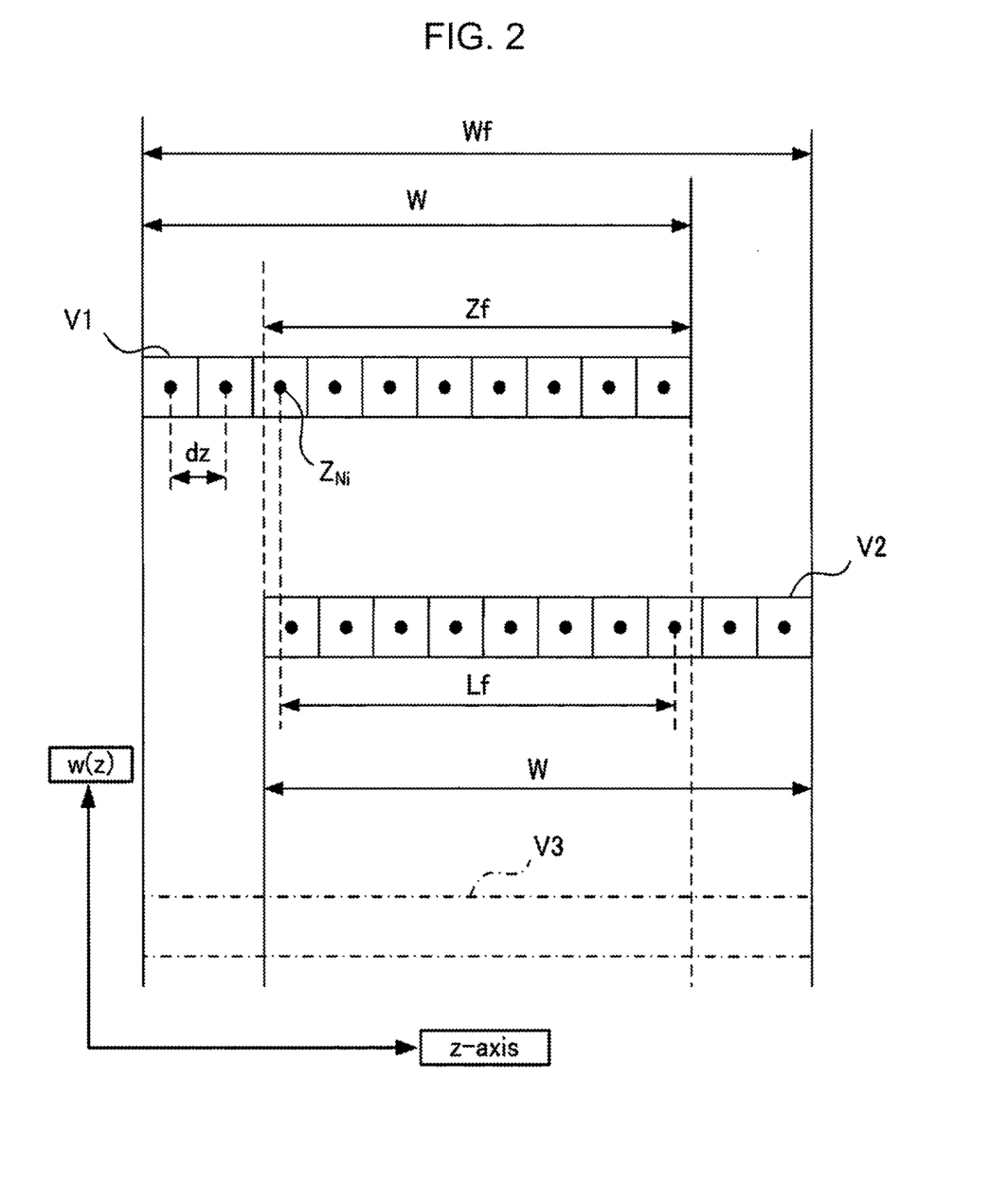
FIG. 2 is a schematic view representing a three-dimensional region of a subject that is scanned by the X-ray CT system as an embodiment.
Figure 3:
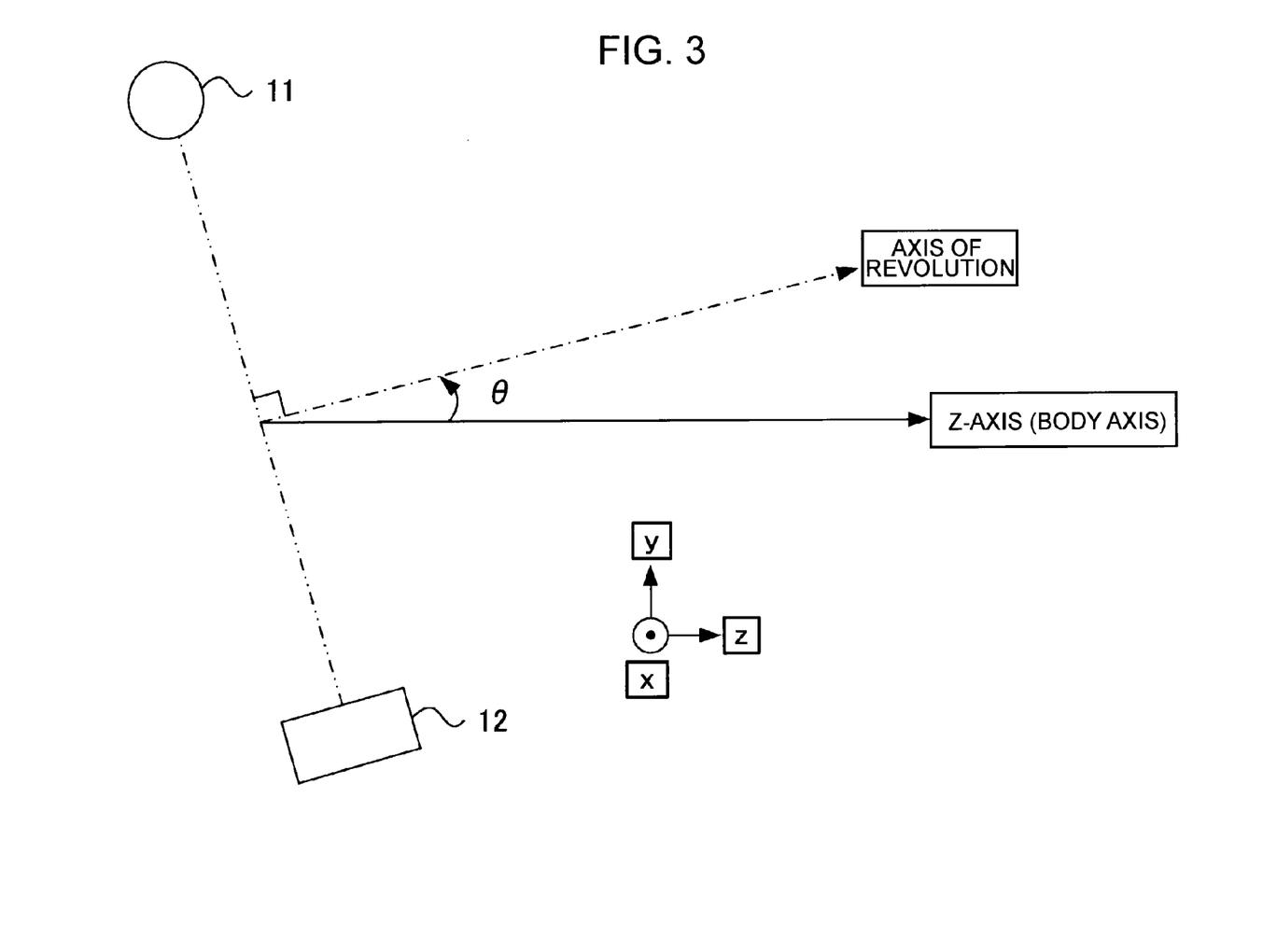
FIG. 3 is a schematic view showing a tilt angle in the X-ray CT system as an embodiment.

FIG. 2 is a schematic view representing the three-dimensional region of the subject E scanned by the X-ray CT system 1 in the rostrocaudal direction of the subject E (in the direction of axis z). FIG. 2 is a view seen in the direction that is perpendicular to axis z and shows one line of pixels which x coordinates and y coordinates share in a first image V1 and a second image V2. Moreover, in FIG. 2, the first image V1 and the second image V2 are shown shifted from each other for the sake of explanation. FIG. 3 is a schematic view showing a tilt angle θ. The processor 15 receives, from the image generator 14, the coordinates of a first pixel in the first image V1, which has been generated of a first three-dimensional region of the subject E by the image generator 14, and the coordinates of a second pixel in the second image V2 generated of a second three-dimensional region of the subject E. The processor 15 then combines the first pixel with the second pixel on a one-for-one basis within a predetermined range in the rostrocaudal direction. The determination of the predetermined range by the processor 15 is based on the tilt angle θ that is defined between the body axis of the subject E and the axis of revolution of the radiator 11 and the detector 12. The tilt angle θ is an angle that results from the execution of a so-called tilt scanning, in which the revolving module 13 is inclined in the direction of y-z plane (i.e., an inclination is made of the plane of revolution of the radiator 11 and the detector 12).

The feathering width Zf of the first image V1 and second image V2 is calculated by the following equation. Here, the feathering width Zf represents the predetermined range, where a third pixel is generated as described later. By the way, the expression (W−Zo) representing the translation distance of the couch 10 is assumed constant notwithstanding the tilt angle θ. In addition, if the tilt angle θ is 0 (i.e., not a tilt scanning), then Zf=Zo in the following equation. In this case, the processor 15 may combine the first pixel with the second pixel on a one-for-one basis for the scanning performed on the condition that the translation distance (W−Zo) of the couch 10 is not divisible by the pixel pitch dz in coordinates.

$$Zf = W - (W - Zo) \times \cos\theta \qquad \text{[Equation 1]}$$

Zo: overlap length [mm]

W: width of the first image V1 and the second image V2 in the z-axis direction [mm]

θ: tilt angle [rad, radians]

In addition, at a predetermined x coordinate and a predetermined y coordinate, the number of pixels N included in the width W in the direction of axis z of the image, the number of pixels Nf used for feathering, and the pixel index Ni as starting point of feathering are calculated by the following equation.

$$N = W/dz$$

$$Nf = CEIL[Zf]/dz$$

$$Ni = N - Nf \qquad \text{[Equation 2]}$$

dz: pixel pitch in coordinates in the direction of axis z
CEIL[X]: integer that results from rounding up "X"

Here, the pixel index Ni as starting point of feathering means that the processor 15 determines pixel combinations in the range from the Ni-th pixel to the N-th pixel of the first image V1 in the direction of axis z with the corresponding pixels of the second image V2.

In addition, the processor 15 calculates, by the following equation, the identification coefficient 'a' that indicates whether the Ni-th pixel of the first image V1 in the direction of axis z closest to the zeroth pixel of the second image V2 in the direction of axis z is positioned in the positive direction or in the negative direction with respect to the zeroth pixel of the second image V2 in the direction of axis z.

$$a = \begin{cases} 1, & \text{if mod } [Zf, dz] < \dfrac{dz}{2} \\ 0, & \text{else} \end{cases} \qquad \text{[Equation 3]}$$

mod[A, B]: remainder that results from the division of A by B

If the identification coefficient 'a' is 0, then the processor 15 designates, as the Ni-th pixel, the pixel of the first image V1 closest in the negative direction to the zeroth pixel of the second image V2 in the direction of axis z. On the other hand, if the identification coefficient 'a' is 1, then the processor 15 designates, as the Ni-th pixel, the pixel of the first image V1 closest in the positive direction to the zeroth pixel of the second image V2 in the direction of axis z.

In this way, the processor 15 combines the Ni-th pixel of the first image V1 with the zeroth pixel of the second image V2, and starting from this combination, the processor 15 makes successive combinations on a one-for-one basis in the direction of axis z.

Moreover, the processor 15 comprises a calculation unit 150, which calculates a weighting factor w for a third pixel with respect to the first pixel and the second pixel, based on the coordinates of the first pixel and the coordinates of the second pixel.

The calculation unit 150 calculates the weighting factor w by the following equation. The weighting factor w is used by the synthesizer 16 for generating a third pixel, which will be described later.

$$w(Z) = \dfrac{Z : -Z_{Ni}^n}{Lf} \qquad \text{[Equation 4]}$$

$$Lf = Zf' + dz - 2 * \text{mod}[Zf', dz]$$

Z: z coordinate of the i-th pixel of an n-th image
W(Z): weighting factor for generating a third pixel (Synthesizer 16)

The synthesizer 16 generates a third pixel from the first pixel and the second pixel, which are set as a combination by the processor 15, and the synthesizer 16 generates a third image V3 that includes the third pixel. In this case, the synthesizer 16 generates a third image V3 as a result of the synthesis executed between the first image V1, which the image generator 14 has generated about the first three-dimensional region of the subject E, and the second image V2, which the image generator 14 has generated about the second three-dimensional region of the subject E. The third image V3 is an image that represents the three-dimensional region that corresponds to the total region Wf covered by the first image V1 and the second image V2. Here, the synthesizer 16 determines coordinates for the third pixel, based on the weighting factor w calculated by the calculation unit 150 as well as on the coordinates of the first pixel and the coordinates of the second pixel.

The synthesizer 16 determines a z coordinate ζ for the third pixel by the following equation.

$$\zeta_{Ni+j+a} = \dfrac{(1 - w(Z_{Ni+j+a}^1)) \cdot Z_{Ni+j+a}^1 + w(Z_j^2) \cdot Z_j^2}{1 - w(Z_{Ni+j+a}^1) + w(Z_j^2)} \qquad \text{[Equation 5]}$$

j: integers from 0 to N

In other words, the smaller the z coordinates of the first pixel and the second pixel used for the synthesis, the nearer the z coordinate ζ of the third pixel to the z coordinate of the first pixel determined by the synthesizer 16. On the other hand, the larger the z coordinates of the first pixel and the second pixel used for the synthesis, the nearer the z coordinate Z of the third pixel to the z coordinate of the second pixel determined by the synthesizer 16. As a result, the coordinates of the first pixel and the second pixel are reflected directly to those of the third pixel depending on the combination used for the synthesis.

In addition, the synthesizer 16 determines a pixel value Q for the third pixel, based on the weighting factor w by the calculation unit 150, the coordinates of the first pixel and the coordinates of the second pixel, and the pixel value of the first pixel and the pixel value of the second pixel.

The synthesizer 16 determines a pixel value Q for the third pixel by the following equation.

$$Q_{Ni+j+a} = \dfrac{(1 - w(Z_{Ni+j+a}^1)) \cdot P_{Ni+j+a}^1 + w(Z_j^2) \cdot P_j^2}{1 - w(Z_{Ni+j+a}^1) + w(Z_j^2)} \qquad \text{[Equation 6]}$$

P=pixel value of the i-th pixel of an n-th image

In other words, the smaller the z coordinates of the first pixel and the second pixel used for the synthesis, the closer the pixel value Q of the third pixel to the pixel value of the first pixel determined by the synthesizer 16. On the other hand, the larger the z coordinates of the first pixel and the second pixel used for the synthesis, the closer the pixel value Q of the third pixel to the pixel value of the second pixel determined by the synthesizer 16. As a result, the pixel values of the first pixel and the second pixel are reflected, depending on their combination, directly to that of the third pixel.

In this way, the synthesizer 16 generates a third pixel for a third image V3, based on the first pixel and the second pixel constituting the combination made by the processor 15, and the synthesizer 16 generates a third image V3 by using only the third pixel within a predetermined range and by using the first pixel and the second pixel in the other ranges. Here, the other ranges are areas that are covered by the first image V1 and the second image V2, excluding the predetermined range. The synthesizer 16 generates the third image V3 by using the first pixel in the area covered by the first image V1 excluding the predetermined range and by using the second pixel in the area covered by the second image V2 excluding the predetermined range.

(Controller 17, Display 18 and Operation Unit 19)

The controller 17 controls the actions of all parts. The controller 17 is configured to include, for example, a processing unit and a storage device. The processing unit comprises, for example, a CPU (Central Processing Unit), a GPU (Graphic Processing Unit), or an ASIC (Application Specific Integrated Circuit). The storage device is configured to include, for example, a ROM (Read Only Memory), a RAM (Random Access Memory), or a HDD (Hard Disc Drive). The storage device stores computer programs for execution of the functions of all parts of the X-ray CT system 1. The processing unit executes these computer programs for realization of the above-mentioned control processes. The operation unit 19 is used by the operator operating the X-ray CT system 1. The display 18 comprises a display device, for example, a liquid crystal display. The operation unit 19 includes various hardware keys (buttons, switches, etc.) provided on the frame or the like of the X-ray CT system 1. In addition, if a touch panel display and a GUI are provided, then the operation unit 19 includes various software keys displayed on the display. Incidentally, the display 18 and the operation unit 19 may be provided interior or exterior to the X-ray CT system 1.

[Actions]

Figure 4:
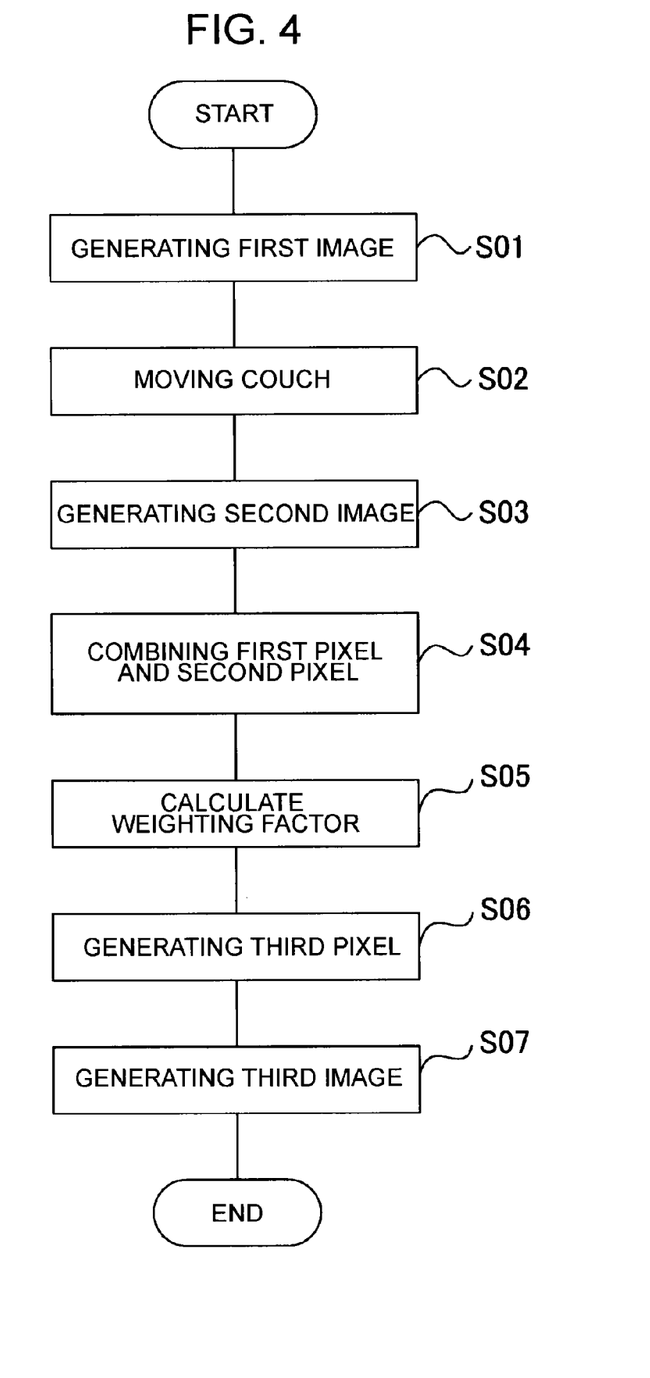
FIG. 4 is a flow chart showing exemplary actions taken by the X-ray CT system as an embodiment.

FIG. 4 is a flowchart showing actions taken by the X-ray CT system 1 as the embodiment.

(S01)

The controller 17 controls the couch 10 to be still, controls the radiator 11 to irradiate the subject E with X-rays, controls the detector 12 to detect X-rays that have passed through the subject E, and controls the image generator 14 to generate a first image V1 of a first three-dimensional region of the subject E.

(S02)

The controller 17 controls the radiator 11 to stop the X-ray radiation, controls the couch 10 to move in the rostrocaudal direction of the subject E and then controls it to stop and stand still.

(S03)

The controller 17 controls the radiator 11 to irradiate the subject E with X-rays, controls the detector 12 to detect X-rays that have passed through the subject E, and controls the image generator 14 to generate a second image V2 of a second three-dimensional region of the subject E.

(S04)

The controller 17 controls the processor 15 to receive the coordinates of a first pixel in the first image V1 and the coordinates of a second pixel in the second image V2 from the image generator 14 and to combine the first pixel and the second pixel on a one-for-one basis within a predetermined range in the rostrocaudal direction.

(S05)

The controller 17 controls the calculation unit 150 to calculate a weighting factor w for the coordinates of a third pixel with respect to the first pixel and the second pixel, based on the coordinates of the first pixel and the coordinates of the second pixel.

(S06)

The controller 17 controls the synthesizer 16 to generate a third pixel for a third image V3, based on the first pixel and the second pixel constituting the combination made by the processor 15.

(S07)

The controller 17 controls the synthesizer 16 to generate a third image V3 by using only the third pixel within a predetermined range and by using the first pixel and the second pixel in the other ranges. As mentioned above, the controller 17 completes the actions shown in FIG. 4.

[Operation and Effects]

Now, the operation and effects of the X-ray CT system 1 as the embodiment are described.

The X-ray CT system 1 comprises a couch 10, a radiator 11, a detector 12, an image generator 14, a processor 15, and a synthesizer 16. The couch 10 is mounted with a subject E and moves it in the rostrocaudal direction of the subject E. The radiator 11 irradiates the subject E mounted on the couch 10 with X-rays. The detector 12 detects X-rays that have passed through the subject E, of the X-rays radiated by the radiator 11. The image generator 13 generates an image that represents a three-dimensional region of the subject E, based on data detected by the detector 12. The processor 15, based on the coordinates of a first pixel in a first image V1 of a first three-dimensional region of the subject E generated by the image generator 14 and the coordinates of a second pixel in a second image V2 of a second three-dimensional region of the subject E generated, combines the first pixel and the second pixel on a one-for-one basis within a predetermined range in the rostrocaudal direction. The synthesizer 16 generates a third pixel from the first pixel and the second pixel constituting the combination by the processor 15 and generates a third image V3 that includes the third pixel. The first pixel and the second pixel having been combined on a one-for-one basis in this way, the third pixel in the predetermined range is made to directly reflect the coordinates and pixel values of the pixels that are the sources to the image generation. This realizes provision of an X-ray CT system and a method of processing medical images that enable combining of a plurality of constituent images with reduced adverse effect, which can otherwise result from the differences in coordinates of the pixels matched in the overlapped areas of the images.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray CT system, comprising:
a couch configured to have a subject mounted thereon and to be translated in the rostrocaudal direction of the subject;
a radiator configured to irradiate the subject mounted on the couch with X-rays;
a detector configured to detect X-rays from the radiator that have passed through the subject;
an image generator configured to generate a first image that represents a first three-dimensional region of the subject and a second image that represents a second three-dimensional region of the subject, based on data detected by the detector;

processing circuitry configured to combine, based on coordinates of first pixels in the first image and coordinates of second pixels in the second image, the first pixels with the second pixels on a one-for-one basis within a predetermined range in the rostrocaudal direction in which a translation distance of the couch is not evenly divisible by a pixel pitch in the coordinates of the first and second images; and a synthesizer configured to generate third pixels relative to the combined first and second pixels, and to generate a third image that includes the third pixels.

2. The X-ray CT system according to claim 1, wherein the synthesizer is configured to generate the third pixels based on the first pixels and the second pixels, and generate the third image by using only the third pixels within the predetermined range, and by using the first pixels and the second pixels in ranges other than the predetermined range.

3. The X-ray CT system according to claim 1, wherein the processing circuitry is further configured to calculate a weighting factor for coordinates of the third pixels with respect to the first pixels and the second pixels, based on the coordinates of the first pixels and the coordinates of the second pixels; and wherein the synthesizer is configured to determine the coordinates of the third pixels, based on the calculated weighting factor, the coordinates of the first pixels, and the coordinates of the second pixels.

4. The X-ray CT system according to claim 1, wherein the processing circuitry is further configured to calculate a weighting factor for coordinates of the third pixels with respect to the first pixels and the second pixels, based on the coordinates of the first pixels and the coordinates of the second pixels; and wherein the synthesizer is configured to determine pixel values for the third pixels, based on the calculated weighting factor, the coordinates of the first pixels, the coordinates of the second pixels, the pixel values of the first pixels, and the pixel values of the second pixels.

5. The X-ray CT system according to claim 1, wherein the processing circuitry is configured to determine the predetermined range based on a tilt angle defined between a body axis of the subject and an axis of revolution of the radiator and the detector.

6. A method of processing medical images including a first image of a first three-dimensional region of a subject and a second image of a second three-dimensional region of the subject, the first and second images having been generated by an X-ray CT system, the X-ray CT system including a couch having the subject mounted thereon and being moved in the rostrocaudal direction of the subject, the method comprising:

combining, based on coordinates of first pixels in the first image and coordinates of second pixels in the second image, the first pixels with the second pixels on a one-for-one basis within a predetermined range in the rostrocaudal direction in which a translation distance of the couch is not evenly divisible by a pixel pitch in the coordinates of the first and second images;

generating third pixels relative to the combined first and second pixels; and generating a third image that includes the third pixels.

7. The X-ray CT system according to claim 1, wherein the processing circuitry is configured to determine the predetermined range based on a tilt angle defined between a body axis of the subject and an axis of revolution of the radiator and the detector.

8. The X-ray CT system according to claim 2, wherein the processing circuitry is configured to determine the predetermined range based on a tilt angle defined between a body axis of the subject and an axis of revolution of the radiator and the detector.

9. The X-ray CT system according to claim 3, wherein the processing circuitry is configured to determine the predetermined range based on a tilt angle defined between a body axis of the subject and an axis of revolution of the radiator and the detector.

10. The X-ray CT system according to claim 4, wherein the processing circuitry is configured to determine the predetermined range based on a tilt angle defined between a body axis of the subject and an axis of revolution of the radiator and the detector.

11. The method of claim 6, wherein the step of generating the third image comprises generating the third image by using only the third pixels within the predetermined range, and by using the first pixels and the second pixels in ranges other than the predetermined range.

12. An X-ray CT system, comprising:

a couch to have a subject mounted thereon and to be translated in the rostrocaudal direction of the subject;

a radiator to irradiate the subject mounted on the couch with X-rays;

a detector to detect X-rays from the radiator that have passed through the subject;

an image generator that generates a first image that represents a first three-dimensional region of the subject and a second image that represents a second three-dimensional region of the subject, based on data detected by the detector;

processing circuitry that combines, based on coordinates of first pixels in the first image and coordinates of second pixels in the second image, the first pixels with the second pixels on a one-for-one basis within a predetermined range in the rostrocaudal direction in which a translation distance of the couch is not evenly divisible by a pixel pitch in the coordinates of the first and second images; and a synthesizer that generates third pixels relative to the combined first and second pixels, and generates a third image that includes the third pixels.

* * * * *